United States Patent

Tanaka et al.

[11] Patent Number: 5,118,472
[45] Date of Patent: Jun. 2, 1992

[54] ANALYTICAL ELEMENT FOR ANALYSIS OF WHOLE BLOOD

[75] Inventors: Mitsutoshi Tanaka; Shigeru Nagatomo; Teppei Ikeda, all of Saitama, Japan

[73] Assignee: Fuji Photo Film Co., Ltd., Kanagawa, Japan

[21] Appl. No.: 216,769

[22] Filed: Jul. 8, 1988

[30] Foreign Application Priority Data

Jul. 8, 1987 [JP] Japan .................. 62-170468

[51] Int. Cl.⁵ .............................. G01N 31/22
[52] U.S. Cl. .............................. 422/56; 422/57; 422/58; 436/170
[58] Field of Search .............. 422/56, 57, 58, 61, 422/101; 436/63, 170, 177, 178; 210/505, 508, 509, 500.26, 500.29, 767

[56] References Cited

U.S. PATENT DOCUMENTS

| | | | |
|---|---|---|---|
| 3,983,005 | 9/1976 | Goodhue et al. | 435/19 X |
| 3,992,158 | 11/1976 | Przybylowicz et al. | 435/11 X |
| 4,042,335 | 8/1977 | Clement | 435/805 X |
| 4,132,650 | 1/1979 | Kirsch et al. | 210/508 X |
| 4,258,001 | 3/1981 | Pierce et al. | 436/170 X |
| 4,637,978 | 2/1987 | Dappen | 422/57 X |
| 4,783,315 | 11/1988 | Arai et al. | 422/57 X |

Primary Examiner—Jill A. Johnston
Attorney, Agent, or Firm—McAulay Fisher Nissen Goldberg & Kiel

[57] ABSTRACT

In an integral multilayer analytical element which comprises a first nonfibrous porous layer, a second nonfibrous porous layer, and a fibrous porous layer superposed in this order to a water-impermeable light-transmissive support, the above three porous layers are integrally laminated to each other substantially closely by an adhesive disposed partially so as to form through microspaces to the degree not to interfere approximately uniform permeation of liquid, a reagent composition to produce an optically detectable change in the presence of an analyte is incorporated into at least one of said three porous layers, the improvement comprising that the void volume and the void volume per unit area of the first nonfibrous porous layer is less than a half of the void volume per the same unit area of the second nonfibrous porous layer. By using the analytical element of the invention, the analytical values of various analytes free from the hematocrit values of blood samples can be obtained from whole blood samples in the range of the hematocrit values of 25% to 55%.

13 Claims, No Drawings

ANALYTICAL ELEMENT FOR ANALYSIS OF WHOLE BLOOD

BACKGROUND OF THE INVENTION

1. Field of the Invention

This invention relates to a dry-type chemical analytical element used for determination of a particular substance in a body fluid, such as, blood.

2. Description of the Prior Art

The quantitative analyses of various metabolic components, such as glucose, bilirubin, urea nitrogen, uric acid, cholesterol, lactate dehydrogenase, creatine kinase, GOT and GPT, are important for clinical field, particularly in the diagnosis of diseases, the follow-up of the course of treatment, the judgement of prognosis and the like. In clinical assays where the sample is blood or the like, it is preferable that a highly accurate assay can be conducted by using a minute amount of liquid sample. In the past, wet methods using a solution of reagent were widely utilized, however they were poor in rapidity.

On the other hand, dry methods are also known such as clinical assay means. The dry method uses an analytical element, such as, a test pieces or a multilayer analytical element, in a substantially dry state where an analytical reagent system is incorporated. The dry methods are superior to the wet methods in terms of simplicity of operation, rapidity, cost, etc. Dry-type multilayer analytical elements have been developed as rapid and accurate assay means, and they are disclosed in U.S. Pat. No. 3,992,158, U.S. Pat. No. 4,292,272, EP 0 162 302A, etc. The dry-type multilayer analytical element is, for example, composed of a transparent support, a reagent layer, a light-reflecting layer, a spreading layer, and the like. The transparent support is a subbed thin plastic film or the like. The reagent layer is coated on the support, and contains the reagent which reacts with the analyte in a liquid sample to develop a color, the optical density of which is proportional to the amount of the analyte. The light-reflecting layer functions to block the light incident into the reagent layer so it does not reach the spreading layer, and to minimize the influence of the liquid sample spotted on the spreading layer at the time of measuring the optical density of the reagent layer. The spreading layer uniformly spreads the liquid sample spotted thereon to a area in proportion to the liquid amount. When quantitative analysis is carried out using the dry-type analytical element, a definite amount of a liquid sample, such as, a whole blood sample is spotted on the spreading layer. The liquid sample spreads in the spreading layer, and passes through the light-reflecting layer. The sample reaches the reagent layer, and reacts with the reagent to form color. After the spotting, the analytical element is incubated for a suitable time at a constant temperature to allow the color reaction to proceed sufficiently. Light is irradiated onto the reagent layer from the side of the transparent support, and reflection optical density is measured at a particular wave length region. The amount of the analyte is determined by using a calibration curve obtained previously.

In the past, the sample to be analyzed is usually blood serum or blood plasma where the erythrocytes are removed, irrespective of whether the wet or dry method is used. However, since the separation of erythrocytes requires labor and equipment cost, analysis is preferably carried out using undiluted whole blood.

When whole blood is analyzed by the dry method, blood cells, i.e. erythrocytes and leukocytes, and other macromolecular components should be separated in the analytical element by some means. For example, the analytical element disclosed in U.S. Pat. No. 3,992,158 is provided with a filtering layer for separating blood cells and other macromolecular components. However, the filtering layer requires a lot of time for the removal of blood cells. Moreover, a part of the analyte is lost in the filtering layer, and thereby, the analysis becomes inaccurate.

Another dry type analytical element utilizable for the analysis of a particular component in whole blood is disclosed in Japanese Patent KOKAI 62-138757 (1987). In the analytical element, erythrocytes in a whole blood sample are separated from plasma in order to remove the interference of the erythrocytes, and moreover, the analyte in the plasma rapidly diffuses into the reagent layer. The analytical element is composed of a first nonfibrous porous layer, a second nonfibrous porous layer and a fibrous porous layer. They are integrally and substantially closely laminated in this order each through an adhesive discontinuously disposed so as to form microspaces continuing through from one layer to the next so as not to interfere with the approximately uniform permeation of liquid. The color forming reagent composition is incorporated into any one of the above three porous layers, and the mean effective pore size of the second nonfibrous porous layer is in the range of 0.8 to 30 $\mu$m. However, when whole blood samples were analyzed by using the above analytical element, the analytical results among the blood samples having the same analyte content varied considerably depending on the hematocrit values (the volume per cent of blood cells in blood).

SUMMARY OF THE INVENTION

An object of the invention is to provide a dry-type analytical element capable of separating erythrocytes in whole blood to avoid their interference with the analytical element, capable of diffusing the analyte in the blood plasma into the reagent layer rapidly, and capable of analyzing the analyte with high accuracy irrespective of the hematocrit value of the whole blood sample.

Such an object has been achieved by an integral multilayer analytical element which comprises a first nonfibrous porous layer, a second nonfibrous porous layer, and a fibrous porous layer superposed in this order onto a water-impermeable light-transmissive support. The above three porous layers are integrally laminated to each other substantially closely by an adhesive discontinuously disposed so as to form microspaces continuing through from one layer to the next so as not to interfere with the approximately uniform permeation of liquid. A reagent composition which produces an optically detectable change in the presence of an analyte is incorporated into at least one of said three porous layers, and the void volume per unit area of the first nonfibrous porous layer is less than a half of the void volume per the same unit area of the second nonfibrous porous layer.

The above object has preferably been achieved, when said reagent composition is incorporated in the first nonfibrous porous layer, or when the effective pore size of the second nonfibrous layer is in the range of 0.8 to 30 $\mu$m.

DETAILED DESCRIPTION OF THE INVENTION

The nonfibrous porous layers are preferably a blushed polymer layer composed of a cellulose ester, such as, cellulose acetate, cellulose acetate/butyrate or cellulose nitrate, disclosed in U.S. Pat. No. 3,992,158 or U.S. Pat. No. 1,421,341. They may be a microporous membrane of polyamide, such as, 6-nylon or 6,6-nylon, polyethylene, polypropylene, or the like, or may be a microporous membrane composed of the polysulfone disclosed in Japanese Patent KOKAI 27006/1987. In addition, they may also be a continuous microspace-containing porous layer where polymer particulates, glass particulates, diatomaceous earth or the like are joined by a hydrophilic or non-water absorptive polymer, such as disclosed in U.S. Pat. No. 3,992,158, and Japanese Patent KOKAI 90859/1980.

The effective pore sizes of the nonfibrous porous layers are the pore size as measured by the bubble point method based upon ASTM F316-70. In the case that the nonfibrous porous layer is a membrane filter composed of a blushed polymer prepared by the phase separation method, liquid paths in the direction of thickness are, in general, the narrowest at the free side surface at the time of the production of the membrane (glossy surface), and the pore size, assuming that the cross section of the liquid path is a circle, is the smallest in the vicinity of the free surface. The pore sizes of the individual liquid paths estimated at the narrowest part along the path with respect to the direction of thickness have a distribution in the direction of the membrane surface, and the maximum value among the varying pore sizes controls the filtration ability for particles. It is usually measured by the bubble point method and is defined as the effective pore size herein. The effective pore size of the first nonfibrous porous layer may be equal to or different from that of the second nonfibrous porous layer. However, the effective pore size of the first nonfibrous porous layer is preferably not larger than three times that of the second nonfibrous porous layer. In addition, the effective pore size of the second nonfibrous porous layer is preferably in the range of 0.8 to 30 $\mu$m.

In the analytical element of the invention, the void volume per unit area of the first nonfibrous porous layer is made less than a half of the void volume of the second nonfibrous porous layer per the same unit area. The void volume of the first nonfibrous porous layer is preferably less than 1 cm$^3$ per 100 cm$^2$. As a method of adjusting the void volume, the thickness of the first nonfibrous porous layer may be made less than one half of that of the second nonfibrous porous layer, where the void contents of both layers is kept equal to each other. Alternatively, the void content of the former may be made less than half of that of the latter, the thicknesses of both layer being equal. The above relation of void volumes may be made by varying both of the thicknesses and the void contents. The void content can be decreased, for example, by treating a membrane with a suitable solvent for the material of the membrane.

In the case of using a membrane filter composed of blushed polymer prepared by the phase separation method, it is preferable that the glossy face is disposed on the support side, of either the first nonfibrous porous layer or the second nonfibrous porous layer.

When the optically detectable change, such as the coloring of or the color change produced in the registration layer, the reagent layer or the like is measured by reflection photometry from the side of the light-transmissive support, the second nonfibrous porous layer shielding the red color of the hemoglobin contained in the erythrocyte of the whole blood sample. It may also function as a light-reflecting layer or background layer. The second nonfibrous porous layer may contain the light-reflective particulates such as titanium dioxide or barium sulfate dispersed therein using a hydrophilic polymer as a binder. Preferable binders are gelatin, gelatin derivatives, polyacrylamide and the like. Light-reflective particulates may also be incorporated into either or both of the first nonfibrous porous layer and the fibrous porous layer.

The second nonfibrous porous layer is joined to the first nonfibrous porous layer by an adhesive. The adhesive is disposed partially or discontinuously so as to form through microspaces so as not to interfere with uniform permeation of the liquid. Such a joining method utilizable for the analytical element of the invention is disclosed in Japanese Patent KOKAI 62-138756 (1987).

The fibrous porous layer is utilized as a spreading layer of the liquid sample spotted on the analytical element, and it has a metering action. The metering action is such that a sample spotted on the spreading layer spreads at a fixed amount per unit area in lateral directions without uneven distribution of any component in the sample. The material constituting the fibrous porous layer may be filter paper, nonwoven fabric, woven fabrics, such as, plain weaves, knitted fabrics, such as, tricot fabric, glass fiber filter paper, etc. Preferable materials for the fibrous porous layer are woven fabrics and knitted fabrics. The woven fabric, etc., may be treated with the glow discharge, such as, disclosed in GB 2,087,074A. The fibrous porous layer may contain a hydrophilic polymer or surfactant as disclosed in EP 0 162 301A and Japanese Patent Application 122875/1986, 122876/1986 and 143754/1986 in order to adjust the spreading area, spreading speed and the like. The fibrous porous layer is joined to the first nonfibrous porous layer by an adhesive in the same manner as described for the first and second non-fibrous layers.

A preferable material of the light-transmissive water impermeable support is polyethylene terephthalate. The material may be a cellulose ester, such as, cellulose triacetate. In order to bind the layer laminated to the support securely, the support is usually provided with an undercoating layer or is made hydrophilic.

The analytical element of the invention may employ various layer constructions referring to the disclosures of U.S. Pat. No. 3,992,158, U.S. Pat. No. 4,292,272 and Japanese Patent KOKAI 62-138756, 62-138757 and 62-138758 (1987). The following embodiments are practically employable as the analytical element of the invention:

(1) The fibrous porous layer, the second nonfibrous porous layer, the first nonfibrous porous layer and the support, superposed in this order.

(2) The fibrous porous layer, the second nonfibrous porous layer, the first nonfibrous porous layer, a binding layer (or a water-absorption layer) and the support, superposed in this order.

(3) The fibrous porous layer, the second nonfibrous porous layer, the first nonfibrous porous layer, a registration layer and the support, superposed in this order.

(4) The fibrous porous layer, the second nonfibrous porous layer, the first nonfibrous porous layer, a reagent layer and the support, superposed in this order.

The support may include a superposed undercoating layer. The registration layer is, in general, the layer where the dye produced in the presence of an analyte diffuses and is optically detected there through the light transmissive support. The registration layer may be composed of a hydrophilic polymer, and it may contain a mordant, for example, a cationic polymer in the case that the dye is anionic. The water-absorption layer is, in general, the layer where the dye produced in the presence of an analyte does not diffuse into it substantially, and it may be composed of a hydrophilic polymer being readily swellable.

The reagent layer, the registration layer, the water-absorption layer or the like may be composed of a hydrophilic polymer. The hydrophilic polymer includes gelatin, its derivatives, such as, phthalated gelatin, cellulose derivatives, such as, hydroxymethyl cellulose, agarose, polyacrylamide, polymethacrylamide and copolymers of acrylamide or methacrylamide and various vinyl monomers.

One or more nonfibrous or fibrous porous layers may be incorporated between the first nonfibrous porous layer and the second nonfibrous porous layer. A barrier layer, a gas-permeable layer, a light-reflecting layer or the like may be incorporated between the reagent layer and the first nonfibrous porous layer in the embodiment (4) mentioned previously. A barrier layer, a light-reflecting layer or the like may be incorporated between the registration layer and the first nonfibrous porous layer in the embodiment (3) mentioned previously. A binding layer for binding the nonfibrous porous layer may be provided on the support, the under coating layer, the water-absorption layer, the registration layer or the like. The binding layer is preferably composed of a hydrophilic polymer capable of binding the porous layer, when it is wet with water to swell, such as, gelatin, gelatin derivatives, polyacrylamide and starch.

The reagent composition includes the compositions capable of producing an optically detectable substance such as a dye in the presence of an analyte. Examples of the reagent composition include the compositions producing a dye by the oxidation of a leuco dye, such as, arylimidazole leuco dyes disclosed in U.S. Pat. No. 4,089,747, Japanese Patent KOKAI 193352/1984, etc., the compositions containing a diazonium salt, a composition containing a compound capable of being coupled to another compound by oxidation to produce a dye, such as, combinations of 4-aminoantipyrines and phenols or naphthols and a composition comprising a compound capable of producing a dye in the presence of a coenzyme in reduced form and an electron carrier. In the case of analytical elements for measuring an enzyme activity, the reagent composition may be comprised of a self-color-developing type substrate capable of releasing a color material, such as, p-nitrophenol. The reagent composition may also contain an enzyme; the examples being described in the specification of Japanese Patent KOKAI 62-138756 (1987) from page 18 to page 20.

The reagent composition may contain an activator, a buffer, a hardening agent, a surfactant and the like. The buffers suitable for the analytical element of the invention are carbonate buffers, borate buffers, phosphate buffers, Good's buffers, and the like. Such a buffer may be selected with reference to "Tanpakushitsu Koso no Kiso-Jikken-Ho (Fundamental Experimental Method of Proteins, Enzymes)" (Horio et al., Nanko-Do, 1981), Biochemistry, vol. 5, No. 2 pp. 467–477, 1966, or the like.

At least, a part of the reagent composition is incorporated into one of the aforementioned three porous layers. All components of the reagent composition may be incorporated into a single porous layer, or they may be divided and incorporated into two or more porous layers. In addition, a part of the components of the reagent composition may be incorporated into the aforementioned layer containing the hydrophilic polymer as a binder.

As the method for incorporating the reagent composition into at least one of the three porous layer, the reagent composition is dissolved or suspended in water or an organic solvent, and immersed into or applied onto the porous layer. Then, the porous layer is bound to another water-permeable layer, such as, a reagent layer, for example, by the method disclosed in U.S. Pat. No. 4,292,272. Instead, the porous layer is first bound to another water-permeable layer, such as, an undercoating layer, a binding layer or a water-absorption layer, and thereafter, the solution or suspension of the reagent composition is applied onto the porous layer. The coating method and the immersing method may be conventional, and the coating method may be selected from dip coating, doctor coating, hopper coating, curtain coating and the like. When a layer containing the reagent composition and a hydrophilic polymer as a binder is coated on the support or the like followed by binding the first nonfibrous porous layer which does not contain the reagent composition thereon by the method disclosed in U.S. Pat. No. 4,292,272 or the like, the reagent composition can substantially be incorporated into the first nonfibrous porous layer.

The analytical element of the invention is particularly effective for the quantitative analysis of the macromolecular components in whole blood, such as, total protein, albumin and various enzymes, the components bound to protein, such as, bilirubin, and the hydrophobic components, such as cholesterol and glycerides as well as the lower molecular components, such as, glucose, urea, uric acid and creatinine. The analytical element can also be used for the determination of an antigen or an antibody by an immunological method by incorporating at least one of an antigen or an antibody into one or more of the porous layers.

By using the analytical element of the invention, the analytical values of various analytes free from the hematocrit values of blood samples can be obtained from whole blood samples in the range of the hematocrit values of 25% to 55%.

EXAMPLES

EXAMPLE 1

The support employed was a colorless transparent polyethylene terephthalate (PET) film having a thickness of 180 $\mu$m on which a gelatin undercoating was provided. An aqueous gelatin solution was coated on the support so as to obtain a dry thickness of 7 $\mu$m, followed by drying to form a water-absorption layer. The surface of the water-absorption layer was moistened uniformly with water at about 25° C., and a cellulose acetate membrane filter having aminimum pore size of 3.0 $\mu$m, a thickness of 70 $\mu$m and a void content of about 80% was laminated thereon, and dried. The following composition 1 and the composition 2 were successively coated, and dried to complete the first nonfibrous porous layer.

| Composition 1 | |
|---|---|
| Gelatin | 0.64 g/m$^2$ |
| Polyoxyethylene nonyl phenyl ether (n = 40) | 2.5 g/m$^2$ |
| Tris(hydroxymethyl)aminomethane | 0.46 g/m$^2$ |
| Potassium dihydrogenphosphate | 0.46 g/m$^2$ |
| L-Aspartic acid | 2.5 g/m$^2$ |
| Magnesium chloride anhydrous | 0.3 g/m$^2$ |
| Peroxidase | 6,400 U/m$^2$ |
| Flavin adenine dinucleotide | 28 mg/m$^2$ |
| Thiamine pyrophosphate | 118 mg/m$^2$ |
| α-Ketoglutaric acid | 500 mg/m$^2$ |
| Oxaloacetate decarboxylase | 12,600 U/m$^2$ |
| Pyruvate oxidase | 35,000 U/m$^2$ |
| pH 7.5, Aqueous solution | |
| Composition 2 | |
| Leuco dye* | 1.8 g/m$^2$ |
| Polyoxyethylene nonyl phenyl ether | 0.6 g/m$^2$ |
| Ethanol solution | |

*2-(3,5-dimethoxy-4-hydroxyphenyl)-4-phenethyl-5-(4-dimethylaminophenyl)-imidazole Starch paste was adhered in the rate of 3 g/m$^2$ as a solid matter in a dot area ratio of about 20% to the surface of another cellulose acetate membrane filter having a minimum pore size of 3.0 μm, a thickness of 140 μm and a void content of about 80% ("Microfilter FM 300", Fuji Photo Film Co., Ltd.) by the screen printing method through a 100 mesh screen. The membrane filter was laminated on the first nonfibrous porous layer, and dried to form the second nonfibrous porous layer. The void volume ratio of the first nonfibrous porous layer to the second nonfibrous porous layer was about 1:2.

Subsequently, a tricot fabric about 250 μm thick composed of PET spun yarn was laminated as the fibrous porous layer onto the second nonfibrous porous layer by the same dot binding method as above, and thereby, the analytical element for measuring glutamin-oxaloacetic transaminase (GOT) activity was completed.

EXAMPLE 2

Another analytical element for measuring GOT activity was prepared in the same manner as Example 1, except for the following modifications to the first nonfibrous porous layer.

Another cellulose acetate membrane filter 140 μm thick having the same effective pore size and void content was used instead of the cellulose acetate membrane filter 70 μm thick.

The treating solution containing an equal weight of methanol and methylenechloride was coated at a rate of 3 m/min. followed by drying prior to coating the composition 1 and the composition 2.

The void content of the membrane filter decreased to about 36% by this treatment. The void volume ratio of the first nonfibrous porous layer to the second nonfibrous porous layer became about 0.9:2.

COMPARATIVE EXAMPLE

Another analytical element for measuring GOT activity was prepared in the same manner as Example 1, except that another cellulose acetate membrane filter 140 μm thick having the same minimum pore side and void content ("Microfilter FM 300", Fuji Photo Film Co., Ltd.) was used instead of the cellulose acetate membrane filter 70 μm thick. The void volume ratio of the first nonfibrous porous layer to the second nonfibrous porous layer was about 1:1.

EXAMPLE OF MEASUREMENT

Six kinds of blood samples were prepared from three fresh whole blood drawn with heparin having a hematocrit value of 25%, 40% and 55% by adding GOT (Sigma Co., U.S.A.) so as to have a GOT activity of 280 and 850 U/l.

Each analytical element was cut into square pieces of 1.5×1.5 cm, and placed in a plastic mount. The above blood sample was spotted onto each analytical element, and incubated at 37° C. The absorbance at 640 nm was measured after 2.5 minutes and 4 minutes from the PET support side by reflection photometry, and respective GOT activities were calculated by using the transmission optical density (ODt) based upon the principle described in Clinical Chemistry, Vol. 24, p. 1335 (1978). The results are shown in Table 1.

TABLE 1

| Analytical Element | GOT U/ml | Hematcrit Value | | |
|---|---|---|---|---|
| | | 25% | 40% | 55% |
| Example 1 | | 305 | 281 | 270 |
| Example 2 | 280 | 294 | 280 | 252 |
| Comparative | | 420 | 260 | 182 |
| Example 1 | | 967 | 855 | 851 |
| Example 2 | 850 | 857 | 851 | 852 |
| Comparative | | 1020 | 843 | 756 |

The above data indicates that the analytical elements of the invention are hardly affected by the hematocrit value of whole blood sample compared with the comparative analytical element.

We claim:

1. In an integral multilayer analytical element which comprises a first nonfibrous porous layer, a second nonfibrous porous layer, and a fibrous porous layer superposed in this order to a water-impermeable light-transmissive support, the above three porous layers being integrally laminated to each other by an adhesive layer discontinuously disposed so as to form microspaces continuing through from one layer to the next so as not to interfere with the approximately uniform permeation of a liquid, a reagent composition to produce an optically detectable change in the presence of an analyte being incorporated into at least one of said three porous layers, the improvement which comprises the void volume per unit area of the first nonfibrous layer being less than half of the void volume per the unit area of the second nonfibrous porous layer and wherein the effective pore size of the first non-fibrous layer is not larger than three times that of the second non-fibrous layer.

2. The analytical element of claim 1 wherein said reagent composition is incorporated into the first nonfibrous porous layer.

3. The analytical element of claim 1 wherein the effective pore size of the second nonfibrous porous layer is in the range of 0.8 to 30 μm.

4. The analytical element of claim 1 wherein the first nonfibrous porous layer is a blushed polymer layer.

5. The analytical element of claim 4, wherein said blushed polymer is cellulose ester.

6. The analytical element of claim 1, wherein the second nonfibrous porous layer is a blushed polymer layer.

7. The analytical element of claim 6 wherein said blushed polymer is cellulose ester.

8. The analytical element of claim 1 wherein both of the first nonfibrous porous layer and the second nonfibrous porous layer are blushed polymer layers.

9. The analytical element of claim 8 wherein said blushed polymer is cellulose ester.

10. The analytical element of claim 1 wherein a registration layer or a water-absorption layer is incorporated between the first nonfibrous porous layer and the support.

11. The analytical element of claim 1 wherein the void volume of the first nonfibrous layer is less than 1 cm$^3$ per 100 cm$^2$.

12. The analytical element of claim 1 wherein the void content of the first and second nonfibrous layers are equal to each other and the first nonfibrous layer is less than half as thick as the second nonfibrous layer.

13. The analytical element of claim 1 wherein the thickness of the first and second nonfibrous layers are equal and the void volume of the first nonfibrous layer is less than one half that of the second nonfibrous layer.

* * * * *